United States Patent [19]

Walker

[11] 4,230,720
[45] Oct. 28, 1980

[54] HETEROCYCLIC DITHIOPHOSPHATES OR PHOSPHONATES AS INSECTICIDES AND ACARICIDES

[75] Inventor: Francis H. Walker, Mill Valley, Calif.

[73] Assignee: Stauffer Chemical Company, Westport, Conn.

[21] Appl. No.: 62,202

[22] Filed: Jul. 30, 1979

[51] Int. Cl.³ .................... A01N 43/24; C07D 319/04
[52] U.S. Cl. .................................. 424/278; 260/338;
260/340.7; 260/340.9 R; 564/209; 424/276;
424/277; 549/30; 549/39
[58] Field of Search ...................... 260/340.7; 424/278

[56] References Cited
U.S. PATENT DOCUMENTS

| | | | |
|---|---|---|---|
| 3,136,784 | 6/1964 | Beriger et al. | 260/340.7 |
| 3,247,223 | 4/1966 | Walsh et al. | 260/340.7 |
| 3,317,561 | 5/1967 | Levy et al. | 260/340.7 |

FOREIGN PATENT DOCUMENTS 1138977 10/1962 Fed. Rep. of Germany ........... 424/278

*Primary Examiner*—Ethel G. Love
*Attorney, Agent, or Firm*—Edwin H. Baker

[57] ABSTRACT

Compounds of the formula

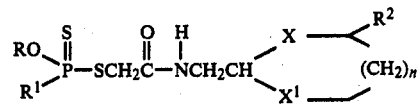

wherein
R is alkyl having 1-4 carbon atoms;
R¹ is alkyl having 1-4 carbon atoms, or alkoxy having 1-4 carbon atoms;
R² is hydrogen or alkyl having 1-4 carbon atoms;
X is oxygen or sulfur;
X¹ is oxygen or sulfur and n is 0, 1 or 2 which are useful as insecticides and acaricides.

6 Claims, No Drawings

HETEROCYCLIC DITHIOPHOSPHATES OR PHOSPHONATES AS INSECTICIDES AND ACARICIDES

DESCRIPTION OF THE INVENTION

This invention relates to certain novel chemical compounds and their use as insecticides and acaricides. More particularly, this invention relates to certain novel heterocyclic dithiophosphates or phosphonates which are useful as insecticides and acaricides.

The compounds of the present invention that are useful as insecticides and acaricides are those having the structural formula $$\begin{array}{c} RO \\ \diagdown \\ R^1 \end{array} \overset{S}{\underset{\parallel}{P}} - SCH_2 \overset{O}{\underset{\parallel}{C}} - \overset{H}{\underset{|}{N}} CH_2 CH \overset{X - CH - R^2}{\underset{X^1 \diagdown}{\diagup}} (CH_2)_n$$

wherein
R is alkyl having 1-4 carbon atoms, preferably ethyl;
$R^1$ is alkyl having 1-4 carbon atoms, preferably ethyl, or alkoxy having 1-4 carbon atoms, preferably ethoxy;
$R^2$ is alkyl having 1-4 carbon atoms, preferably methyl, or hydrogen;
X is oxygen or sulfur;
$X^1$ is oxygen or sulfur and n is 0, 1 or 2.

In the above description of the compounds of this invention, alkyl includes both straight chain and branched chain configurations, for example, methyl, ethyl, n-propyl, isopropyl, n-butyl, iso-butyl or tert. butyl.

The compounds of the present invention are prepared by the following general method.

Reaction No. 1

$$ClCH_2 - \overset{O}{\underset{\parallel}{C}} - Cl + H_2NCH_2(OCH_3)_2 + NaOH \longrightarrow$$
$$ClCH_2 \overset{O}{\underset{\parallel}{C}} - \overset{H}{\underset{|}{N}} CH_2CH(OCH_3)_2 + NaCl$$

Generally, a mole amount of aminoacetaldehyde dimethyl acetal and a mole amount of sodium hydroxide as an aqueous solution are mixed in a solvent such as dichloromethane. Then a mole amount of chloroacetyl chloride is added dropwise to the mixture with stirring at 0°–10° C. Thereafter, the mixture is allowed to heat to room temperature and is stirred for one hour. The mixture is washed with water, sodium carbonate and water followed by drying and evaporation to yield the desired reaction product.

Reaction No. 2

$$ClCH_2\overset{O}{\underset{\parallel}{C}}-\overset{H}{\underset{|}{N}}CH_2CH\overset{OCH_3}{\underset{OCH_3}{\diagdown}} + \overset{HX-CH-R^2}{\underset{HX^1-CH}{\diagdown}}(CH_2)_n \xrightarrow{\text{acid cat.}}$$
$$ClCH_2\overset{OH}{\underset{\parallel}{C}}NCH_2CH\overset{X-CH-R^2}{\underset{X^1-CH}{\diagdown}}(CH_2)_n + 2CH_3OH$$

wherein X, $X^1$, $R^2$ and n are as defined.

Generally, a mole amount of the amide reaction product of Reaction No. 1, a mole amount of the glycol and about 0.2 mole of a strong acid catalyst such as 2-naphthalenesulfonic acid dihydrate are dissolved in a solvent such as dichloroethane, mixed in a reaction vessel fitted with a variable tape-off distillation head attached to the column. The reaction mixture is heated to reflux with stirring and the distillate is removed at its boiling temperature around 83° C.

The reaction mixture is then cooled to room temperature and stirred for 15 minutes with potassium carbonate. The mixture is then filtered and the filtrate passed through a small amount of Florisil ®. The filtrate is evaporated to yield the desired reaction product.

Reaction No. 3

$$RO\overset{S}{\underset{\underset{R^1}{|}}{\overset{\parallel}{P}}}-SJ + ClCH_2\overset{O}{\underset{\parallel}{C}}-\overset{H}{\underset{|}{N}}CH_2CH\overset{X-CH-R^2}{\underset{X^1\diagdown}{\diagup}}(CH_2)_n \xrightarrow{DMF}$$

$$RO\overset{S}{\underset{\underset{R^1}{|}}{\overset{\parallel}{P}}}-SCH_2\overset{O}{\underset{\parallel}{C}}-\overset{H}{\underset{|}{N}}CH_2CH\overset{X-CH-R^2}{\underset{X^1\diagdown}{\diagup}}(CH_2)_n + JCl$$

wherein R, $R^1$, $R^2$, X, $X^1$ and n are as defined and J is potassium or ammonium.

Generally, a slight excess of the potassium or ammonium salt of the dithioyl phosphate or phosphonate and the chloroacetamide are stirred together in dimethyl formamide as a solvent first at room temperature for about four hours and than at about 50° C. for an additional four hours. At the end of this time, the mixture is diluted with toluene, washed with a brine solution, dried and evaporated to yield the desired reaction product.

Preparation of the compounds of this invention is illustrated by the following examples.

EXAMPLE I

N-(2,2-dimethoxyethyl)chloroacetamide $$ClCH_2\overset{O\ H}{\underset{\parallel\ |}{C N}}CH_2CH(OCH_3)_2$$

This examples teaches a method of preparation for the reactant N-(2,2-dimethoxyethyl)chloroacetamide.

A mixture of 105.1 grams (g) (1.0 mole) of aminoacetaldehyde dimethyl acetal, 80 g (1.0 mole) of a 50% aqueous solution of sodium hydroxide, and 200 milliliters (ml) dichloromethane are placed in a one liter flask fitted with a stirrer and thermometer. To this is added 113.0 g (1.0 mole) of chloroacetyl chloride dropwise with rapid stirring at 0°–10°. After the addition is complete, the reaction is allowed to rise to room temperature and is stirred for one hour. Next, the mixture is washed with 100 ml water, 100 ml sodium carbonate solution and 100 ml water, followed by drying and evaporation to give 113.8 g (63% yield) of the title compound, m.p. 33°–36° C.

EXAMPLE II 2-(chloroacetylamino)methyl-1,3-dioxolane

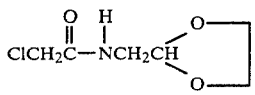

This examples teaches the preparation of an intermediate compound.

A mixture of 36.0 g (0.2 mole) of N-(2,2-dimethoxyethyl)chloroacetamide, 12.4 g (0.2 mole) of ethylene glycol and 0.2 g of 2-naphthalene sulfonic acid dihydrate in 150 ml dichloroethane are placed in a 500 ml flask to which a variable tape-off distillation head, the thermometer and stirrer are attached. The mixture is heated to reflux and distillate is removed at a head temperature of 83° C. A total of 54.1 g of distillate is collected. The mixture is then cooled to room temperature and then stirred for 15 minutes with 10 g of solid potassium carbonate. The mixture is next filtered and the filtrate passed through a small amount of Florisil ®. The filtrate is then evaporated to leave a liquid, 26.2 g (73% yield) $n_D^{30}$ 1.4921, identified as the title compound by nuclear magnetic resonance.

EXAMPLE III

O,O-diethyl-S-[N-(1,3-dioxolane-2-yl)-methylaminoacetyl]dithiophosphate

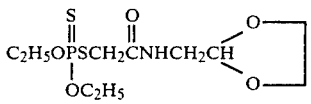

This examples teaches the synthesis of a compound of this invention.

6.0 g (0.0297 mole) ammonium salt of diethyldithiophosphate and 100 ml dimethylformamide were added to a 200 ml round bottom flask equipped with a magnetic stirrer and thermometer. 4.8 g (0.027 mole) of the dioxolane compound prepared in Example II was added and the mixture stirred for 12 hours and allowed to stand overnight. The reaction product was warmed to 45° C. for three hours with stirring and taken up in 100 ml toluene and washed three times with brine. The organic phase was dried with MgSO$_4$, filtered and the solvent removed in a rotary vacuum, yielding 2.0 g of the desired compound $n_D^{30}$ 1.5277. The structure was confirmed by nuclear magnetic resonance and infrared spectroscopy.

The following is a table of certain selected compounds that are preparable according to the procedure described hereto. Compound numbers are assigned to each compound and are used through the remainder of the application.

TABLE 1

$$\underset{R^1}{\overset{RO}{>}}\overset{S}{\underset{\|}{P}}-SCH_2\overset{O}{\underset{\|}{C}}-\overset{H}{\underset{|}{N}}CH_2\overset{X}{\underset{X^1}{C}}\underset{(CH_2)_n}{\overset{R^2}{<}}$$

| Compound Number | R | R$^1$ | R$^2$ | X | X$^1$ | n | $n_D^{30}$ or m.p. |
|---|---|---|---|---|---|---|---|
| 1 | C$_2$H$_5$ | C$_2$H$_5$ | CH$_3$ | O | O | 1 | 62–70° C. |
| 2 | C$_2$H$_5$ | C$_2$H$_5$ | H | O | O | 1 | 89–92° C. |
| 3 | C$_2$H$_5$ | C$_2$H$_5$ | H | O | O | 2 | 46–49° C. |
| 4 | C$_2$H$_5$ | C$_2$H$_5$ | CH$_3$ | O | O | 0 | 45–48° C. |

TABLE 1-continued

| Compound Number | R | R$^1$ | R$^2$ | X | X$^1$ | n | $n_D^{30}$ or m.p. |
|---|---|---|---|---|---|---|---|
| 5 | C$_2$H$_5$ | C$_2$H$_5$ | H | S | O | 0 | 54–58° C. |
| 6 | C$_2$H$_5$ | C$_2$H$_5$ | H | S | S | 0 | 51–53° C. |
| 7 | C$_2$H$_5$ | C$_2$H$_5$O | H | O | O | 0 | 1.5280 |
| 8 | C$_2$H$_5$ | C$_2$H$_5$O | H | O | O | 1 | 74–77° C. |

INSECTICIDAL EVALUATION TESTS

The compounds of Table I were found to have insecticidal activity against the following insect species which were used in the evaluation tests described hereafter.

1. Housefly (HF) - *Musca domestica* (Linn.)
2. Black Bean Aphid (BBA) - *Aphis fabae* (Scop.)
3. Green Peach Aphid (GPA) - *Myzus persicae* (Sulzer)

The insecticidal evaluation tests were conducted as follows:

Housefly: Test compounds were diluted in acetone and aliquots pipetted onto the bottom of 55×15 mm aluminum dishes. To insure even spreading of the chemical on the bottom of the dishes, one ml of acetone containing 0.02% peanut oil was also added to each dish. After all solvents had evaporated, the dishes were placed in circular cardboard cages containing 25 female houseflies, one to two days old. The cages were covered on the bottom with cellophane and on top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The LD$_{50}$ values are expressed below in Table II under the heating "HF", in terms of μg of the test compound per 25 female flies.

Black Bean Aphid: Nasturtium plants (*Tropaeolum* sp.), approximately five cm tall, were transplanted into sandy loam soil in three-inch clay pots and infested with 25–50 black bean aphids of mixed ages. Twenty-four hours later they were sprayed to the point of runoff with 50–50 acetone-water solutions of the test chemicals. Treated plants were held in the greenhouse and mortality was recorded after 48 hours. Test concentrations ranged from 0.05% down to that at which 50% mortality occurred. LD$_{50}$ values are expressed below in Table II under the heading "BBA" in terms of percent of the test compound in the sprayed solution.

Green Peach Aphid: Radish plants (*Rhaphanus sativus*), approximately two cm tall, were transplanted into sandy loam soil in three-inch clay pots and infested with 25–50 green peach aphids of mixed ages. Twenty-four hours later they were sprayed to the point of runoff with 50—50 acetone-water solutions of the test chemicals. Treated plants were held in the greenhouse and mortality was recorded after 48 hours. Test concentrations ranged from 0.05% down to that at which 50% mortality occurred. LD$_{50}$ values are expressed below in Table II under the heading "GPA" in terms of the percent of the test compound in the sprayed solution.

ACARICIDAL EVALUATION TEST

The two-spotted mite (2SM), Tetranychus urticae (Koch), was employed in tests for miticides. The test procedure was as follows:

Pinto bean plants (Phaseolus sp.), approximately 10 cm. tall, were transplanted into sandy loam soil in three-inch clay pots and thoroughly infested with two-spotted mites of mixed ages and sexes. Twenty-four hours later, the infested plants were inverted and dipped for two-three seconds in 50—50 acetone-water solutions of the test chemicals. Treated plants were held in the greenhouse, and seven days later mortality was determined for both the adult mites and the nymphs hatching from eggs which were on the plants at the time of treatment. Test concentrations ranged from 0.05% down to that at which 50% mortality occurred. $LD_{50}$ values are expressed below in Table II under the headings "2SM-PE" (i.e., post-embryonic) and "2SM-Eggs", in terms of percent concentration of the test compound in the solution.

TABLE 2

| Compound Number | HF (μg) | BBA (%) | GPA (%) | 2SM-PE (%) | 2SM-EGGS (%) |
| --- | --- | --- | --- | --- | --- |
| 1 | 100 | .0005 | .002 | .005 | .03 |
| 2 | * | .0005 | .0005 | .01 | ** |
| 3 | 52 | .001 | .001 | .01 | ** |
| 4 | 38 | .002 | .0005 | .01 | ** |
| 5 | 100 | .0008 | .002 | .002 | .008 |
| 6 | 65 | .002 | .0005 | .003 | .03 |
| 7 | 100 | .001 | .002 | ** | ** |
| 8 | * | .005 | .005 | .03 | ** |

\* = Not active at 100 μg and not tested at higher concentrations.
\*\* = Not active at 0.05% and not tested at higher concentrations.

The compounds of this invention are generally formulated into a form suitable for convention application. For example, the compounds can be prepared into a pesticidal composition in the form of emulsions, suspensions, solutions, dusts or aerosol sprays. In general, such pesticidal compositions will contain, in addition to the active compound, the inert adjuvants which are found normally in pesticide preparations. In these compositions, an active compound of the invention can be employed as the sole pesticide component or it can be used in an admixture with other compounds having similar utility.

The pesticide compositions of this invention can contain, (a) liquid adjuvants, such as organic solvents, sesame oil, xylene range solvents, heavy petroleum, etc.; water; (b) emulsifying agents; (c) surface active agents; (d) solid adjuvants such as talc; pyrophyllite, diatomite; gypsum; clays or (e) propellants, such as dichlorodifluoromethane, etc.

If desired, however, the active compounds can be applied directly to the feedstuffs, seeds, etc., or upon other materials upon which the pests feed. In connection with the activity of the presently disclosed pesticidal compounds, it should be fully understood that it is not necesssary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art.

Generally, the active pesticide compound will be embodied in the form of a liquid composition; for example, an emulsion, suspension, or aerosol spray. While the concentration of the active compound in the aforesaid compositions can vary within wide limits, ordinarily the active compound will comprise between about 1.0 and about 95% by weight of the pesticidal composition and more preferably between about 5%–80% by weight

I claim:

1. Compounds having the structural formula $$\begin{array}{c}RO\\ R^1\end{array}\!\!\!\!\underset{\|}{\overset{S}{P}}\!-\!SCH_2\underset{\|}{\overset{O}{C}}\!-\!\underset{|}{\overset{H}{N}}CH_2CH\!\!\underset{X^1}{\overset{X}{\diagdown}}\!\!\!\!\!\!\overset{R^2}{\underset{(CH_2)_n}{<}}$$

wherein
R is alkyl having 1–4 carbon atoms;
$R^1$ is alkyl having 1–4 carbon atoms, or alkoxy having 1–4 carbon atoms;
$R_2$ is hydrogen or alkyl having 1–4 carbon atoms;
X is oxygen;
$X^1$ is oxygen and n is 1.

2. A compound according to claim 1 wherein R is ethyl, $R^1$ is ethyl, $R^2$ is methyl, X is oxygen, $X^1$ is oxygen and n is 1.

3. A compound according to claim 1 wherein R is ethyl, $R^1$ is ethyl, $R^2$ is hydrogen, X is oxygen, $X^1$ is oxygen and n is 1.

4. A compound according to claim 1 wherein R is ethyl, $R^1$ is ethoxy, $R^2$ is hydrogen, X is oxygen, $X^1$ is oxygen and n is 1.

5. The method of controlling insects comprising applying to the habitat thereof an insecticidally effective amount of a compound of the formula $$\begin{array}{c}RO\\ R^1\end{array}\!\!\!\!\underset{\|}{\overset{S}{P}}\!-\!SCH_2\underset{\|}{\overset{O}{C}}\!-\!\underset{|}{\overset{H}{N}}CH_2CH\!\!\underset{X^1}{\overset{X}{\diagdown}}\!\!\!\!\!\!\overset{R^2}{\underset{(CH_2)_n}{<}}$$

wherein
R is alkyl having 1–4 carbon atoms;
$R^1$ is alkyl having 1–4 carbon atoms, or alkoxy having 1–4 carbon atoms;
$R^2$ is hydrogen or alkyl having 1–4 carbon atoms;
X is oxygen;
$X^1$ is oxygen and n is 1.

6. The pesticidal composition comprising a pesticidally effective amount of a compound of the formula $$\begin{array}{c}RO\\ R^1\end{array}\!\!\!\!\underset{\|}{\overset{S}{P}}\!-\!SCH_2\underset{\|}{\overset{O}{C}}\!-\!\underset{|}{\overset{H}{N}}CH_2CH\!\!\underset{X^1}{\overset{X}{\diagdown}}\!\!\!\!\!\!\overset{R^2}{\underset{(CH_2)_n}{<}}$$

wherein
R is alkyl having 1–4 carbon atoms;
$R^1$ is alkyl having 1–4 carbon atoms, or alkoxy having 1–4 carbon atoms;
$R^2$ is hydrogen or alkyl having 1–4 carbon atoms;
X is oxygen;
$X^1$ is oxygen and
n is 1 and an inert carrier therefor.

* * * * *